United States Patent [19]

Skulan

[11] 4,002,731
[45] Jan. 11, 1977

[54] DIAGNOSTIC PROCESS USING SODIUM TYROPANOATE

[75] Inventor: Thomas W. Skulan, Valatie, N.Y.

[73] Assignee: Sterling Drug Inc., New York, N.Y.

[22] Filed: June 17, 1974

[21] Appl. No.: 479,634

[52] U.S. Cl. .................................. 424/5; 424/35; 424/362

[51] Int. Cl.² ................... A61K 29/02; A61K 9/22

[58] Field of Search .................. 424/5, 35

[56] References Cited

UNITED STATES PATENTS

| | | | |
|---|---|---|---|
| 1,815,902 | 7/1931 | Ellzey | 424/5 X |
| 2,436,270 | 2/1948 | Schwenk et al. | 424/5 X |
| 2,790,748 | 4/1957 | Papa et al. | 424/5 |
| 2,801,203 | 7/1957 | Leb et al. | 424/35 X |
| 2,895,988 | 7/1959 | Archer et al. | 424/5 X |
| 3,042,715 | 7/1962 | Obendorf et al. | 424/5 X |
| 3,133,863 | 5/1964 | Tansey | 424/35 X |
| 3,144,479 | 8/1964 | Obendorf | 424/5 X |
| 3,184,386 | 5/1965 | Stephenson | 424/35 X |
| 3,226,431 | 12/1965 | Felder et al. | 424/5 X |

OTHER PUBLICATIONS

Koehler et al., Radiology, vol. 108, pp. 517–519, Sept. 1973.
Fischer et al., Investigative Radiology, vol. 9, pp. 24–31 (No. 1, Jan. – Feb. 1974).

Primary Examiner—Albert T. Meyers
Assistant Examiner—Vera C. Clarke
Attorney, Agent, or Firm—Thomas L. Johnson; B. Woodrow Wyatt

[57] ABSTRACT

Divided doses or sustained release formulations of sodium tyropanoate upon oral administration provide adequate gallbladder visualization with substantially lower blood levels than are obtained with conventional single dose administration.

3 Claims, No Drawings

DIAGNOSTIC PROCESS USING SODIUM TYROPANOATE

This invention relates to a new diagnostic process and new formulation used therein, and in particular is concerned with a new procedure for oral cholecystography and a sustained release formulation employed therein.

Sodium tyropanoate [sodium beta-(3-butyramido-2,4,6-triiodophenyl)-alpha-ethylpropionate] is the most recent addition to the armamentarium of oral cholecystographic agents (U.S. Pat. No. 2,895,988). Other oral cholecystographic agents still commercially available are iopanoic acid [beta-(3-amino-2,4,6-triiodophenyl)-alpha-ethylpropionic acid], and ipodate [beta-(3-dimethylaminomethyleneamino-2,4,6-triiodophenyl)propionic acid] and its sodium and calcium salts.

Although the foregoing oral cholecystographic agents are relatively non-toxic substances, adverse reactions such as minor gastrointestinal disturbances or allergic reactions are occasionally observed. Therefore, it is highly desirable, in order to minimize the occurrence of these undesirable side-effects, to use as low a dose as possible and maintain the blood plasma iodine concentration at the lowest possible level without sacrificing adequate visualization of the gallbladder.

The conventional cholecystographic procedure comprises oral administration of a single dose of contrast agent (25–100 milligrams per kilogram of body weight) sufficient to produce adequate visualization of the gallbladder at the time of maximum concentration of iodine in the gallbladder (about 10–16 hours after administration). Shortly after administration of the contrast agent there is an initial surge in blood iodine levels to a relatively high concentration, followed by a gradual decrease.

It has now been found that in cholecystographic procedures using sodium tyropanoate, if the latter is administered not in a single dose but on the same quantity distributed over a period of time ranging from about 4 to about 10 hours, there is a significant decrease in the maximum blood iodine levels observed with no appreciable decrease in the maximum contrast medium density obtained in the gallbladder X-ray photographs, as compared with the conventional single dose regimen. This phenomenon is not observed with the other cholecystographic agents, iopanoic acid and ipodate.

The process of the invention thus comprises administering orally to a mammalian organism possessing a gallbladder, continuously or intermittently over a period of between about 4 and about 10 hours, a diagnostically effective amount of sodium tyropanoate, whereby a concentration of iodine in the gallbladder sufficient to provide adequate visualization of the gallbladder is obtained, while maintaining the maximum iodine concentration in the blood significantly lower than the maximum iodine concentration in the blood obtained by oral administration of an initial single dose of the same total amount of sodium tyropanoate.

The sodium tyropanoate can be administered in several divided doses (intermittent administration) or in a sustained or controlled release formulation (continuous administration). The total dose of sodium tyropanoate is preferably between 25 and 100 milligrams per kilogram of body weight.

In the divided dose regimen the sodium tyropanoate is preferably administered in from three to six approximately equally divided doses at approximately equal intervals over a period of between 4 and 10 hours. In man maximum gallbladder contrast medium density is obtained about fourteen hours after the initial administration; and maximum iodine blood levels occur after about 6 or 7 hours, said maximum being only about 65% that of the maximum iodine blood levels obtained about 2 hours after administration of a single undivided dose.

When the sodium tyropanoate is administered in sustained release form it is given as a single undivided dose containing sufficient contrast agent to provide adequate X-ray visualization of the gallbladder. The contrast medium is continuously gradually released in the gastrointestinal tract over a period of up to about 10 hours, and the iodine blood levels are at all times significantly below those obtained after administration of a single undivided dose of sodium tyropanoate not formulated for sustained release.

Sustained or controlled release formulations are known in the art (Remington's Pharmaceutical Sciences, 14th Edition, Chapter 89, pp. 1702–1711). They comprise a mixture or coating of the active ingredient with an additive or additives which slow down the release and absorption of the drug or diagnostic agent in the gastrointestinal tract so as to extend the action of the active ingredient over a desired length of time.

Appropriate additives for the sustained release preparations are high molecular weight and polymeric substances. These include various cellulose derivatives, e.g. ethylcellulose, methylcellulose, carboxymethylcellulose, hydroxypropylcellulose and the like; higher molecular weight acids, esters and salts thereof, e.g. alginic acid, metal salts of higher fatty acids, glyceryl esters of higher fatty acids, carnauba wax, beeswax, spermaceti, hydrogenated castor oil, and the like; and synthetic polymers, e.g. polyvinylpyrrolidine, polyvinyl alcohol, polyethylene glycol, carboxyvinyl polymer and the like.

The sustained release preparations are prepared by coating granules, beads or pellets of the active ingredient with one or more additives such as those named above. A preferred type of sustained release preparation of the present invention comprises a granulation of sodium tyropanoate coated with a cellulose derivative. Other additives such as hydrogenated castor oil may be present. The weight of total additives, not including other excipients and binders such as talcum, lactose, starch, Avicel (microcrystalline cellulose), is about 5% of the weight of the sodium tyropanoate.

The sustained release preparation of sodium tyropanoate is conveniently prepared for use in unit dosage form, in tablets or capsules, each unit comprising about 250 and 1000 milligrams of sodium tyropanoate. If desired the sustained release form can be mixed with up to about one-third uncoated sodium tyropanoate in the event a greater initial absorption of the contrast medium is desired while retaining the advantages of the sustained release.

In addition to the advantage of the sustained release preparation in producing lower blood iodine levels, it has also been found that the acute oral toxicity in mice of the sustained release preparation of sodium tyropanoate was significantly less than that of commercial, uncoated sodium tyropanoate.

The following clinical and laboratory data will further illustrate the invention without the latter being limited thereby.

A divided dose study with sodium tyropanoate (commercial BILOPAQUE, uncoated) was carried out in nine humans, all healthy males and females between 20 and 30 years of age. Each individual received the following three regimes, one regimen given each week in random order for a 3-week period:

|  | Hours | | | |
|---|---|---|---|---|
|  | 0 | 2 | 4 | 6 |
| Regimen A: | 3 grams | Placebo | Placebo | Placebo |
| Regimen B: | 750 mg | 750 mg | 750 mg | 750 mg |
| Regimen C: | 375 mg | 375 mg | 375 mg | 375 mg |

Regimen A is the conventional mode of administration except for the placebo doses. Regimens B and C are true divided doses. The drugs were double-blinded and all possible variables, e.g. equipment, diet, etc. were well controlled insofar as possible. X-ray visualization of the gallbladder was performed at 4, 7, 14 and 24 hours after the first capsules were taken. Each film was read blind, independently, by three different radiologists and the Average Cholecystographic Index (ACI) recorded. The ACI is a numerical scoring plan measuring the density of the gallbladder shadows based on the following criteria: 0 (none), 1 (poor), 2 (fair), 3 (good), 4 (excellent); cf. Hoppe et al., Am. J. Roentgen. Rad. Therap. Nuc. Med. 69, 620–7 (1953). The ACI values for the nine subjects were as follows:

| Dose Regimen | Hours Postmedication | | | |
|---|---|---|---|---|
|  | 4 | 7 | 14 | 24 |
| A | 1.4 | 2.4 | 3.5 | 0 |
| B | 1.0 | 2.3 | 3.5 | 0 |
| C | 0.0 | 1.0 | 2.4 | 0 |

The ACI values for Regimen A (single 3 gram dose) and Regimen B (3 gram divided dose) were almost identical indicating that the divided dose could provide adequate visualization.

The average plasma iodine concentrations in micrograms per milliliter in the nine subjects are given in the following table:

| Dose Regimen | Hours Postmedication | | | | | |
|---|---|---|---|---|---|---|
|  | ½ | 1 | 2 | 4 | 7 | 24 |
| A | 10.8 | 77.3 | 125.0 | 104.5 | 55.2 | 18.9 |
| B | 9.7 | 25.2 | 24.5 | 57.5 | 81.8 | 16.8 |
| C | 2.9 | 9.5 | 9.9 | 19.8 | 45.8 | 7.5 |

The data show that the maximum plasma iodine level with Regimen B (divided 3 gram dose), 81.8 µg/ml at 7 hours, was substantially lower than the maximum level with Regimen A (single 3 gram dose), 125.0 µg/ml at 2 hours. This lowering of plasma iodine levels was consistent in all nine subjects. The lowering of serum uric acid with Regimen A and B was almost identical.

In a second study, four different dosage regimens of sodium tyropanoate (commercial BILOPAQUE, uncoated) were evaluated in four healthy subjects, as follows:

|  | Hours | | | | | |
|---|---|---|---|---|---|---|
|  | 0 | 1 | 2 | 3 | 4 | 5 |
| Regimen A: | 3 gram | Placebo | Placebo | Placebo | Placebo | Placebo |
| Regimen B: | 500 mg | 500 mg | 500 mg | 500 mg | 500 mg | 500 mg |
| Regimen C: | 2 gram | Placebo | Placebo | Placebo | Placebo | Placebo |
| Regimen D: | 333 mg | 333 mg | 333 mg | 333 mg | 333 mg | 333 mg |

The four different dosage regimens were given in a blind crossover fashion at 2 week intervals. The order of administration was as follows:

| Volunteer | Regimen | | | |
|---|---|---|---|---|
|  | Week 1 | Week 3 | Week 5 | Week 7 |
| 1 | A | B | C | D |
| 2 | B | C | D | A |
| 3 | C | D | A | B |
| 4 | D | A | B | C |

Blood samples for organic bound iodine determinations were obtained from each subject at 0, 2, 4, 6, 7, 9, 11, 14, 18, 24 and 48 hours after drug ingestion from time zero of dosage schedule.

Urinary pH, volume and iodine concentration levels were determined at 24, 48 and 72 hours from time zero of dosage on each subject.

Radiographs were obtained at 4, 7, 11 and 14 hours from time zero of each regimen on all subjects.

The results for each medication regimen for blood iodine levels, total urinary iodine excretion over a 72-hour period postmedication, and radiological appraisal of gallbladder visualization at 4, 7, 11 and 14 hours postmedication are presented as averages for the four subjects in the following table:

| Results at Hours Post-Medication | Regimen | | | |
|---|---|---|---|---|
|  | A (3 gram - single dose) | B (3 gram - divided dose) | C (2 gram - single dose) | D (2 gram - divided dose) |
| BLOOD IODINE - µg/ml | | | | |
| 0 | 0.18 | 0.20 | 0.20 | 0.35 |
| 2 | 127.93 | 54.08 | 86.30 | 24.38 |
| 4 | 87.40 | 58.60 | 61.25 | 58.48 |
| 6 | 56.70 | 88.18 | 31.98 | 57.15 |
| 7 | 52.35 | 87.85 | 25.03 | 47.53 |
| 9 | 34.23 | 57.73 | 21.35 | 29.60 |
| 11 | 26.78 | 44.30 | 20.10 | 23.88 |

-continued

| Results at Hours Post-Medication | Regimen | | | |
|---|---|---|---|---|
| | A (3 gram - single dose) | B (3 gram - divided dose) | C (2 gram - single dose) | D (2 gram - divided dose) |
| 14 | 23.60 | 31.10 | 17.55 | 19.50 |
| 18 | 23.83 | 26.25 | 16.90 | 15.05 |
| 24 | 19.08 | 20.15 | 14.25 | 10.78 |
| 48 | 11.08 | 9.52 | 5.35 | 6.40 |
| URINE IODINE - mg/d | | | | |
| 24 | 373.28 | 459.63 | 336.10 | 170.00 |
| 48 | 175.55 | 188.83 | 146.33 | 127.60 |
| 72 | 100.00 | 78.70 | 60.85 | 84.10 |
| | 648.83 | 727.16 | 543.28 | 381.70 |
| X-RAY ACI (0-4) | | | | |
| 4 | 2.8 | 1.0 | 2.2 | .5 |
| 7 | 3.2 | 2.4 | 2.5 | 1.0 |
| 11 | 3.7 | 2.9 | 2.3 | 2.2 |
| 14 | 3.6 | 3.7 | 2.6 | 2.1 |

The peak blood iodine level for the 3-gram divided dose (Regimen B), 88.18 µg/ml at 6 hours, is substantially lower (30%) than the peak blood iodine level with the single 3-gram dose (Regimen A), 127.93 µg/ml at 2 hours. Both regimens produced equivalent good to excellent visualization at 14 hours. Comparing Regimen C (2-gram single dose) and Regimen D (2-gram divided dose), the peak blood iodine level in Regimen D is 32% less than in Regimen C with essentially adequate visualization at 11 and 14 hours on a comparative basis.

Sustained release preparations of sodium tyropanoate can be prepared by conventional procedures, illustrated as follows:

Sodium tyropanoate (11,250 grams) and 1,238 grams of Avicel were wet granulated with de-ionized water, then extruded and pelletized and dried at 50° C. The dried pellets were classified with No. 16 and No. 30 mesh screens. The pellets passing the No. 16 screen but retained on the No. 30 screen were retained for coating.

Hydrogenated castor oil (Castorwax MP 70) (466.9 grams) and ethylcellulose (233.1 grams) were dissolved in an equal volume mixture of methylene dichloride and acetone to a total volume of 7000 milliliters with gentle heating and agitation. This solution was spray-dried upon the sodium tyropanoate-Avicel pellets until the weight of coating was 5% that of the weight of sodium tyropanoate and at the same time dusted with talcum so that the amount of talcum was 2.4% that of the sodium tyropanoate.

The resulting coated granulation of sodium tyropanoate was mixed with 8.6% by weight (based on the sodium tyropanoate) of a pelletized excipient granulation prepared from 3 parts by weight of lactose and 1 part by weight each of starch and Avicel, and the final mixture was encapsulated in hard gelatin capsules at 635 milligrams total weight per capsule, each capsule thus containing 500 milligrams of sodium tyropanoate which was confirmed by analysis. Each capsule thus had the following composition:

| Formulation I | |
|---|---|
| Sodium tyropanoate | 500.0 mg |
| Microcrystalline cellulose (Avicel) | 63.6 |
| Hydrogenated castor oil | 16.7 |
| Ethylcellulose | 8.3 |
| Talcum | 12.0 |
| Lactose | 25.8 |
| Starch | 8.6 |
| | 635.0 mg |

The acute oral toxicity in mice of the foregoing formulation was determined, and a 7-day $LD_{50}$ value of 5042 (3623–6596) mg/kg in terms of sodium tyropanoate was obtained. This compared to a $LD_{50}$ value of 3158 (1302–3900) for commercial sodium tyropanoate capsule mix (uncoated). The sustained release preparation was thus statistically significantly less toxic than the immediate-release material.

Similar sustained-release preparations were prepared wherein the ethylcellulose was replaced by methylcellulose.

A further formulation was prepared containing 375 milligrams of sustained-release sodium tyropanoate and 125 milligrams of immediate-release sodium tyropanoate, with the following composition:

| Formulation II | |
|---|---|
| Controlled-release pellets | |
| Sodium tyropanoate | 375.0 mg |
| Microcrystalline cellulose (Avicel) | 41.3 |
| Hydrogenated castor oil | 12.5 |
| Ethylcellulose | 6.2 |
| Talcum | 9.0 |
| Immediate-release pellets | |
| Sodium tyropanoate | 125.0 mg |
| Microcrystalline cellulose (Avicel) | 13.75 |
| Excipient pellets | |
| Lactose | 31.35 mg |
| Starch | 10.45 |
| Microcrystalline cellulose (Avicel) | 10.45 |
| | 635.0 mg |

The sustained-release formulations were tested in male and female cats weighing 2.5 to 3.5 kg by oral administration at a dose level of 100 mg/kg as sodium tyropanoate, and the gallbladder visualization Cholecystographic Index (CI) and blood iodine levels (µg/ml) were determined at selected time intervals by standard methods. Parallel studies were carried out on immediate-release (uncoated) sodium tyropanoate preparations. The results are given in the following table:

| Group | Formulation | Dose mg/kg as Na Tyropanoate | Number of Cats | TIME 0 CI | TIME 0 $I_2$ | ½ Hour CI | ½ Hour $I_2$ |
|---|---|---|---|---|---|---|---|
| I. | Na Tyropanoate 80 mesh powder (control) | 100 | 6 | 0 | 0 | 0 | .102 |
| II. | Na Tyropanoate granulated uncoated | 100 | 5 | 0 | 0 | 0 | .101 |
| III. | Formulation 1 Controlled Release (all drug coated) | 100 | 6 | 0 | 0 | 0 | .021 |
| IV. | Na Tyropanoate 80 mesh powder (uncoated) plus Na Tyropanoate (coated) | 33 plus 67 | 9 | 0 | 0 | 0 | .034 |

| Group | 1 CI | 1 $I_2$ | 2 CI | 2 $I_2$ | 4 CI | 4 $I_2$ | 7 CI | 7 $I_2$ | 24 CI | 24 $I_2$ |
|---|---|---|---|---|---|---|---|---|---|---|
| I. | 0.2 | .167 | 1.6 | .154 | 3.1 | .069 | 4.0 | .025 | 4.0 | .006 |
| II. | 0.6 | .137 | 1.4 | .153 | 2.6 | .092 | 3.8 | .033 | 4.0 | .007 |
| III. | 0.5 | .060 | 0.8 | .061 | 1.8 | .024 | 2.8 | .023 | 3.3 | .007 |
| IV. | 0.4 | .058 | 1.4 | .092 | 3.1 | .033 | 4.0 | .018 | 4.0 | .006 |

The results showed that the uncoated sodium tyropanoate formulations (Groups I and II) and the sustained release formulations (Groups III and IV) all gave good to excellent visualization after seven hours, and that iodine blood levels with the sustained release formulations (Groups III and IV) were markedly lower at all times than with the uncoated formulations (Groups I and II). After 24 hours the blood iodine had essentially disappeared for all groups.

Sodium tyropanoate in a divided dose regimen was compared with the chemically related iopanoic acid and its sodium salt in a divided dose regimen as follows: Sodium tyropanoate, iopanoic acid and sodium iopanoate were administered orally at 100 mg/kg to groups of 30 cats. The three compounds were also administered to groups of five cats in divided doses of 20 mg/kg, five times, at 2-hour intervals. X-rays were taken at one-half, 1, 2, 4, 7 and 24 hours post-medication and the gallbladder shadows were assayed by Cholecystographic Index (CI). Blood samples were collected at the same time intervals and the organic bound iodine determined. The results are given in the following table:

| Compound | Dose in mg/kg | No. of Cats | 0 | ½ | 1 | 2 | 4 | 7 | 24 |
|---|---|---|---|---|---|---|---|---|---|
| Sodium tyropanoate | 100 | 30 | 0 | 0 | 0.5 | 1.6 | 3.1 | 3.7 | 3.9 |
| | 20/2Hr. × 5 | 5 | 0 | 0 | 0.4 | 1.8 | 3.0 | 3.6 | 4.0 |
| Iopanoic acid | 100 | 30 | 0 | 0 | 0 | 0 | 0.2 | 1.2 | 3.6 |
| | 20/2Hr. × 5 | 5 | 0 | 0 | 0 | 0 | 0 | 0.8 | 2.8 |
| Sodium iopanoate | 100 | 30 | 0 | 0 | 0 | 0 | 0.6 | 1.7 | 3.7 |
| | 20/2Hr. × 5 | 5 | 0 | 0 | 0 | 0 | 0 | 0.8 | 3.6 |

(Average Cholecystographic Index (CI) — Hours Post-Medication)

| Compound | Dose in mg/kg | 0 | ½ | 1 | 2 | 4 | 7 | 24 |
|---|---|---|---|---|---|---|---|---|
| Sodium tyropanoate | 100 | 0 | 84 | 110 | 129 | 110 | 65 | 28 |
| | 20/2Hr. × 5 | 0 | 24 | 21 | 21 | 36 | 63 | 27 |
| Iopanoic acid | 100 | 0 | 6 | 24 | 66 | 142 | 208 | 127 |
| | 20/2Hr. × 5 | 0 | 21 | 35 | 65 | 106 | 166 | 216 |
| Sodium iopanoate | 100 | 1 | 38 | 93 | 204 | 365 | 383 | 230 |
| | 20/2Hr. × 5 | 0 | 28 | 39 | 73 | 193 | 345 | 296 |

(Microgm. Compound/ml Plasma — Hours Post-Medication)

The foregoing data again show that the maximum blood levels obtained with the divided dose regimen of sodium tyropanoate were much less, about one-half, than the maximum levels obtained with an equivalent single initial dose, whereas the quality of visualization was essentially the same. By contrast, iopanoic acid and its sodium salt were not only much slower in producing adequate visualization, but there was no significant difference in the maximum blood levels obtained whether administered in one initial dose or in divided doses.

I claim:

1. A process which comprises administering orally to a mammal possessing a gallbladder, single undivided dose in a sustained or controlled release formulation or intermittently over a period of between about four and about ten hours, an amount of sodium tyropanoate of between about 25 and 100 milligrams per kilogram of body weight of the mammal, whereby a concentration of iodine in the gallbladder sufficient to provide adequate X-ray visualization of the gallbladder is obtained, while maintaining the maximum iodine concentration in the blood significantly lower than the maximum iodine concentration in the blood obtained by oral administration of an initial single dose of the same total amount of sodium tyropanoate.

2. The process according to claim 1 in which the sodium tyropanoate is administered in from three to six approximately equally divided doses at approximately equal intervals over a period of between 4 and 10 hours.

3. A process which comprises administering orally to a mammal possessing a gallbladder a sustained release formulation comprising an amount of sodium tyropanoate of between about 25 and 100 milligrams per kilogram of body weight of the mammal, whereby a concentration of iodine in the gallbladder sufficient to provide adequate X-ray visualization of the gallbladder is obtained while maintaining the maximum iodine concentration in the blood significantly lower than the maximum iodine concentration in the blood obtained by oral administration of the same amount of sodium tyropanoate alone.

* * * * *

UNITED STATES PATENT AND TRADEMARK OFFICE
CERTIFICATE OF CORRECTION

PATENT NO. : 4,002,731

DATED : January 11, 1977

INVENTOR(S) : Thomas W. Skulan

It is certified that error appears in the above-identified patent and that said Letters Patent are hereby corrected as shown below:

Column 3, line 8, "regimes" should read --regimens--.

Column 8, line 38, Claim 1, --a-- should be inserted before "single".

Signed and Sealed this

Fifth Day of April 1977

[SEAL]

Attest:

RUTH C. MASON
*Attesting Officer*

C. MARSHALL DANN
*Commissioner of Patents and Trademarks*